(12) United States Patent
Alvi

(10) Patent No.: US 6,816,794 B2
(45) Date of Patent: Nov. 9, 2004

(54) APPARATUS AND METHOD FOR DETECTING CONTAMINATION OF OBJECT BY A METAL

(75) Inventor: Khalid Naser Alvi, Halifax (GB)

(73) Assignee: Videojet Technologies, Inc., Wood Dale, IL (US)

(*) Notice: Subject to any disclaimer, the term of this patent is extended or adjusted under 35 U.S.C. 154(b) by 0 days.

(21) Appl. No.: 10/181,046

(22) PCT Filed: Jan. 10, 2001

(86) PCT No.: PCT/GB01/00080
§ 371 (c)(1),
(2), (4) Date: Nov. 18, 2002

(87) PCT Pub. No.: WO01/51959
PCT Pub. Date: Jul. 19, 2001

(65) Prior Publication Data
US 2003/0105600 A1 Jun. 5, 2003

(30) Foreign Application Priority Data
Jan. 12, 2000 (GB) .............................. 0000566

(51) Int. Cl.⁷ .............................................. G06F 19/00
(52) U.S. Cl. ......................................... 702/35; 702/38

(58) Field of Search ................................ 702/57, 33–36, 702/38, 65, 72, 152, 175, 183, 189

(56) References Cited

U.S. PATENT DOCUMENTS 6,636,827 B2 * 10/2003 Sakagami .................... 702/193

* cited by examiner

Primary Examiner—Marc S. Hoff
Assistant Examiner—Craig Steven Miller
(74) Attorney, Agent, or Firm—McAndrews, Held & Malloy

(57) ABSTRACT

The present invention provides apparatus for interactively observing metal or other electrolyte contamination of a product against a reference datum or calibration signal for that product; and modifying the datum signal on line to reflect changes in tolerances between the calibration and observed signals. The method can be used to optimise the calibration signal for a given product; or can be used to identify specific contaminants based upon their effect on the calibration signal. The invention enables an operator to optimise the calibration signal inter actively and thus reduce inaccuracies in the detection of contaminated products due to incorrect tolerances between the calibration and observed signals.

20 Claims, 1 Drawing Sheet

APPARATUS AND METHOD FOR DETECTING CONTAMINATION OF OBJECT BY A METAL

The present invention relates to an apparatus and method, notably to apparatus for inspecting products for contamination and to a method for operating such apparatus.

BACKGROUND TO THE INVENTION

Many products, notably foodstuffs, are inspected as they are produced or packaged to detect metallic impurities therein which might be harmful to the quality of the products and/or to a user of the product, notably if they were to be ingested. Its is therefore customary to pass such products through or past some form of metal detection device. Typically, such devices comprise two, three or more wire coils through one of which, the emitter coil, a pulsed or varying electric current is passed. This causes induction effects to be generated between the coils and an induced current to flow in the other, receptor, coil(s), which can be monitored using any suitable technique. Although, such devices usually operate with an emitter coil inducing a current flow in the other, receptor, coils, there have been proposals in which electric currents flow in each of the coils and it is the interaction of the induction effect, for example the change in phase and/or amplitude on the current flowing in one coil due to the effect of the other coil, which is monitored. Typically, the coils are generally planar circular loops of electric conductor located with the planes of the coils substantially parallel to one another upon a common axis. However, the coils may be of squared, triangular or other plan shape. If desired, ferrite rods or discs can be located within the coils or other means, for example a metal housing for the coils, can provided to shape the inductive field generated by the emitter coil and/or the object can be observed through an aperture in a metal or other screen so as to optimise the sensitivity of the receptor coil to changes caused by the presence of metals adjacent the device and to limit the area of the object scanned to reduce edge effects, for example to avoid scanning thinner edges of the object.

For convenience, the term metal detector will be used herein to denote any such device which monitors a change in the coupling effect between two coils, through at least one of which a pulsed or varying current is passed, in response to the proximity of a metal to the coils. Many forms of metal detectors are commercially available and used in detecting metal contamination of products.

If a metallic object passes adjacent the coils, the coils electrically couple with the object and the inductive effect of one coil on the other changes. Typically, the presence of a metallic object causes a change in the phase of the current induced in the receptor coil which can be observed. This effect is also noted where the metallic object is an electrolyte, for example the gravy or sauce in which solid food particles are carried. For convenience, the term metallic contamination of an object will be used herein to denote in general any electrolyte, metal or other material present in that object which causes a change in the signal produced by a metal detector when that object is located adjacent to the metal detector.

Typically, the object to be observed is passed generally parallel to the plane of the coils of the metal detector. However, if desired, the plane of the coils can be inclined to the line of travel of the object past the metal detector. Alternatively, the object can pass though the plane of the coils, usually axially through the loop of the coils. The term pass will be used hereinafter in respect to moving objects relative to the coils of a metal detector to denote passage through or parallel to the plane of the coils or at any angle intermediate these lines of passage.

In use, an operator passes a series of objects corresponding to the object to be observed past the metal detector. The passage of these objects will cause a series of references signals to be generated, whose characteristic amplitude, phase angle or other features can be determined, for example as a series of digital pulses or numbers defining the amplitude, phase and phase angle of the signal. Such characteristic, or reference signals can then be used to identify subsequent objects moved past the metal detector. The generation of the reference signals may also be carried out using a batch of samples of the actual objects to be observed and which are known to meet the metal contamination criteria for an acceptable product. In this case, slightly varying signals may be observed for each sample due to minor variations in the composition of the objects within each batch. The signals are averaged to produce the characteristic reference signal for the objects within each batch of samples.

The reference signal corresponding to an object is stored in a computer memory or other machine readable storage device so that it can be called up for comparison against the signal from another object of the same type passing the metal detector. Provided that the signal from the other object is, within acceptable limits, the same as the reference signal, the operator will know that the other object also meets the metal contamination requirements set for the calibration object. It is therefore customary to set up the signal stored in the memory to allow for an acceptable variance from the reference signal corresponding to manufacturing tolerances for the object to be observed. Such a signal incorporating such tolerances will be denoted hereinafter as the calibration signal for that product. As indicated above, it is also customary to carry out the calibration with a number of samples and to take the average of the signals from those samples to generate the calibration signal for that type of object.

It has been proposed that the computer controlling the storage and monitoring of the observed signals should carry out an averaging of the observed signals from a series of the same type of object so as to determine whether any optimisation of an initial calibration signal can be made having regard to the limits to acceptability laid down by the operator of the production line or process producing the objects to be observed. Such automated setting up and review of the calibration signal can be carried out at the initial start up of the production of the objects and/or can be carried out as an on-going process during the passage of the stream of objects past the detector.

However, the operator of the production line for the objects has little or no input in the control of the setting of the calibration signal or of the automatic setting up and optimisation of the calibration signal during the object observation process. Typically, the manufacturer of the metal detector will install the detector and will set up the initial limits within which the signal from the detector is to be treated as relating to an acceptable product on the basis of initial samples provided to him by the operator of the object production process and on the basis of tolerances for variation of the metal contamination permitted by the operator. These factors are incorporated into the software controlling the computer which carries out the automatic setting up and optimisation of the calibration signal. All of this requires expert operators and is time consuming.

In view of the complexity of the shape of signal which is generated by the metal detector, the area over which a signal is deemed to be acceptable is formulated as a box-like image and the limits of an acceptable signal are given in terms of the co-ordinates of the box and the general phase angle of that box to a datum line, for example the notional x axis of a display of the signal. The operator is provided with a two or three line display of alphanumeric symbols defining these features so that he can monitor the operation of the metal detector and verify that he has selected the correct calibration signal for use with a given object. However, once the limits of an acceptable signal have been set, the operator has little opportunity to vary the box within which an acceptable signal must lie, other than to switch between the box for one product to the box required for a different product. Furthermore, the automatic setting up and calibration process requires a skilled operator to set it up, the setting up is complex and time consuming and the results are prone to inaccuracies.

We have now devised an apparatus and method for operating it which provides the operator with the ability to over-ride the autoset program and to impose operator determined settings easily and accurately for the variables which determine the co-ordinates within which an acceptable signal must lie. This enables the operator to optimise the boundary to the box-like envelope of the calibration signal having regard to his practical experience and to do this on line during the passage of objects past the detector. The apparatus of the invention also allows an operator to determine why a specific object has been rejected and to take remedial action which would not be possible with the prior metal detection systems. Since the calibration and observed signals from the metal detector are displayed visually, preferably as superimposed images, the comparison of the signals and optimisation of the calibration signal can be carried out by less skilled operators and interactively, resulting in simpler and more accurate optimisation of the calibration signal.

SUMMARY OF THE INVENTION

Accordingly, the present invention provides apparatus for detecting contamination of an object by a metal or other electrolyte, characterised in the apparatus comprises:

a. A mechanism for transporting the object relative to a scanning station at which the object is to be scanned;

b. A metal detector located at the scanning station and adapted to scan the object and to generate an observed signal corresponding to the effect of metal contamination present in the object on the signal generated from the metal detector;

c. Computer means for comparing the observed signal from the metal detector with a calibration signal corresponding to an object having an acceptable level of metal contamination and for identifying when an observed signal received from the metal detector deviates by an unacceptable amount from that calibration signal;

d. Display means for displaying in visual graphical form the observed signal from the metal detector and the calibration signal; and e. Means, for example a keyboard, for use by an operator for varying the calibration signal displayed on the display means.

As stated above, the invention provides a method for adjusting the envelope of the calibration signal for an acceptable object on-line in replacement of the automatic setting up and optimisation processes used hitherto. In this method an operator views the displays, preferably simultaneously, of the observed signals from the metal detector scanning an object and the calibration signal for an acceptable level of metal contamination for that object. These signals are typically in the form of complex loop like images whose form and orientation are characteristic of the object being observed by the metal detector. The operator can adjust the shape and orientation of the calibration signal by inputting control data from the keyboard or other input means so as to optimise the calibration signal with respect to the observed signals for that object. Since he can readily perceive from the visual display whether modification of a particular variable results in a calibration signal which does not provide sufficient latitude between the observed signals and the calibration signal to accommodate manufacturing tolerances, he can readily exclude impractical modifications. Also, he can readily perceive whether a particular modification of a variable results in excessive latitude between the observed and calibration signals, which could result in acceptance of objects which exceed the desired tolerances.

Such simple visual verification of the effect of altering variables in adjusting the calibration signal is not possible with the limited alphanumeric displays available hitherto. The apparatus and method of the invention thus give the operator greater flexibility in adjusting the calibration signal for a given type of object. Moreover, non-skilled operators can readily carry out such adjustment since the results of any adjustment are readily visible on the display device. Furthermore, since each metallic contaminant will usually give rise to a characteristic change in the observed signal, it is possible to build up a library of the characteristic signals for each type of contamination. These can be held in the machine readable storage memory of the computer controlling the operation of the monitoring of signals from the metal detector. Thus, when an object is rejected because its observed signal falls outside the envelope of the calibration signal, the operator can with experience estimate what type of contamination has caused the rejection. His estimation can be verified by superimposing the signal for that contamination on the calibration signal for the object and assessing whether the combined signal is similar to the one which caused rejection of the object. This facility may enable an operator to identify a problem in the production process and to remedy that rapidly, for example to detect extraneous metal particles, such as coins, metal shavings or metal components of the processing equipment, which may have fallen into a foodstuff during its preparation or packaging.

However, many products may deliberately contain metal in some form or another, for example as an electrolyte provided for example by the fats or cooking or other salts present in a foodstuff. In this case, the calibration signal corresponds to the background level of the signal from the foodstuff and this will usually be of a typical shape and phase angle for that product.

For convenience, the invention will be described hereinafter in terms of a package of a foodstuff as the object to be scanned which contains electrolytes which give the package a typical background signal from the metal detector which acts as the calibration signal.

As stated above, due to variations in materials and manufacturing processes, there will usually be some variation in the signal which the metal detector generates from packages of the same foodstuff, even within the same production batch. The operator therefore specifies acceptable variations about the ideal for the product composition and these are used to produce the envelope about the ideal signal which determines the calibration signal for an acceptable product.

The establishment of the calibration signal against which subsequent packages of the foodstuff are compared can be done using conventional techniques. However, the operator can then apply the benefits of his experience in adjusting the dimensions, shape and orientation of the envelope of the calibration signal to optimise the envelope. For example, he may know that the signal from an acceptable product does not vary significantly over certain areas of the envelope, whereas a small deviation in the product composition has a much larger effect on the signal in other areas of the envelope. Thus, he can adjust the boundary of the envelope of the calibration signal in the first case to a tighter percentage variation, for example ±1%, whereas the variation in the boundary in the second case needs to be as much as ±5%. Such assessment of the possible optimisation of the boundary of the envelope is not possible with the two or three line alphanumeric displays used hitherto.

Furthermore, the prior art methods define the envelope for the calibration signal for an acceptable product as a box-like shape, since the computing power required to calculate a complex curved boundary would be uneconomically large and would require complex programming. However, the human eye can readily define the differences between one curved line and another on a visual display. Hence, the operator can define areas in which the boundary can be varied so as to cut out areas where a very large variation in signal is permitted by drawing a line across a corner of the box-like envelope generated by prior art systems using an autoset process. Where a touch screen display is used, it may be possible to permit the operator to draw a boundary which is substantially congruent to the envelope of the reference signal for a product, thus defining a substantially uniform permitted variation from the desired signal over the whole boundary of the envelope of the calibration signal. However, for simplicity, the invention will be described hereinafter in terms of varying the envelope of a calibration signal which is displayed as a generally rectangular envelope on the signal display means.

The metal detector for use in the present invention may take any suitable form and many such are commercially available. Thus, the detector may be a coil type metal detector as described above and the coils of the detector may be placed both to one side of the line of travel of the package to be scanned, with their planes substantially parallel to the line of travel of the package. However, if desired, the coils can be placed one to each side of the path of the package or orientated with the plane of the coils normal to the line of travel of the package to be scanned with the line of travel passing through the loop of the coils of the detector. The coils may also be placed above or below the line of travel of the package, for example when it is desired to scan a product from above so as to minimise the effect of an open topped metal, for example an aluminum foil, container in which the product is contained. The reduction in coupling effect of the coils on each other due to the introduction of the attenuating effect of the package between them is then monitored, notably where the signal generated by the emitter coil is in the radio frequency. For convenience, the invention will be described hereinafter in terms of a metal detector comprising two substantially parallel coils located both to one side of the path of travel of the packages and through the emitter coil of which a current oscillating at a frequency of up to 1 MHz or more, typically 10 to 500 KHz, for example from 25 to 50 KHz in the case of a foodstuff. The optimum value for the amplitude and frequency of such an oscillating current can be readily determined using known techniques for each type of product to be scanned.

As is customary, the packages will be carried past a stationary metal detector upon a conveyor belt or other transport means. However, it is within the scope of the present invention for the package to remain stationary and for the metal detector to be moved across the surface of the package. For convenience, the invention will be described hereinafter in terms of a static metal detector scanning products travelling on a belt, roller or other type of conveyor.

The scanning station can be provided with other features to enhance the operation of the metal detector. Thus, for example the metal detector may have a metal or other screen located between it and the package to be scanned and the detector scans the package through an aperture in the screen. Such an apertured screen defines the area of the package which the detector scans so that possible variations in the signal due to edge effects in the package are minimised. It is particularly preferred to ensure that the package is scanned over approximately from 50 to 90% of its area presented to the scanner and the aperture in the screen can be adjusted in known manner to achieve this. It is also preferred to provide means which detects when the package is located in the desired position with respect to the metal detector. Such means can take the form of a contact or non-contact proximity switch which detects when the leading edge of the package is at a given point in its travel so that the package is in register with the aperture. Such switches include photocells, toggles switches and the like, which actuate an electrical signal at the moment when the leading edge of the package passes a predetermined point. The electrical signal can actuate the metal detector so that the detector operates only when a package is in position to be scanned; or can actuate capture of the signal from a continuously operating metal detector. It is also desirable that the scanning station incorporates guide means which assist consistent orientation of the package as is passes the metal detector and consistent spacing of the package from the metal detector. For example, the conveyor or other transport means can be provided with guide rails at the scanning station which guide the package into a given orientation and position as it passes past the metal detector. If desired, such guide means may incorporate a turntable or other means by which the package can be rotated so that it can be scanned from various directions by the metal detector. This may enable metallic contaminants which have small dimensions in one sense, but large dimensions in others, for example a flat metal washer or a length of wire, to be detected due to the larger amplitude signal generated in one orientation whereas the signal generated in another orientation may be too small to cause the observed signal to fall outside the envelope of the calibration signal.

As stated above, the signal from the metal detector is fed to a computer whose function is to assess the observed signal with respect to the calibration signal, to display that assessment graphically on a visual display means and to alert the operator when the observed signal from a package falls outside the envelope of the calibration signal. Typically, the computer will incorporate software to generate a graphic display of the observed and calibration signals and a look up memory containing the calibration signals for a number of products. Such computers, programs and memories can be of conventional nature, design and operation.

The computer interfaces with a visual display unit, for example a cathode ray tube, a liquid crystal display, a CCD array, a light emitting polymer or other suitable device which generates a visible graphical display of both the observed signal from the metal detector and the calibration signal from the memory unit of the computer. Typically, the calibration signal will be displayed whenever an observed signal is displayed. Typically, the two signals will be superimposed upon one another to facilitate perception of the configuration, size, orientation and shape of the observed signal relative to the calibration signal. However, this need not be the case and the display of either or both signals may occur only when required by the operator, for example in response to the pressing of a given key in the control panel as detailed below. In this latter case, the computer will incorporate the necessary software to compare the observed signal and the calibration signal and to generate a suitable alarm or other signal when the observed signal falls outside the limits of the calibration signal. Typically, the computer will actuate a mechanism for pushing or otherwise rejecting a contaminated package from the transport mechanism so that it does not proceed further along the packaging or other process. If desired, such rejected packages can be diverted to a side conveyor or bin in which they are held in the order in which they were rejected and the computer can incorporate additional or other storage means whereby the observed signal for that rejected package can be stored for subsequent examination by the operator of the apparatus. Thus, the operator can relate the rejected package to its observed signal and determine what the nature of the contamination was as indicated above.

As stated above, the computer interfaces with a control keypad, panel or other means whereby the operator can select the calibration signal against which a given package or series of packages are to be assessed and can vary the calibration signal displayed in the visual display unit to optimise the calibration signal. As indicated above, this control means may be provided by a touch screen facility on the visual display unit which permits the operator to call up a selected calibration signal and to vary that upon the screen. However, it will usually be preferred to provide a keypad by which the operator can achieve these functions.

The operator can use the keypad to call up onto the visual display unit the calibration signal for a specified package type from the memory unit of the computer. This can then be adjusted on the screen by applying corrective factors using the keypad. For example, the operator can vary the percentage tolerance which can be accepted for one of the variables of the contents of the package. Thus, the operator may decide that the salt content of the contents of the package is usually closely defined and that a tolerance of only ±1% can be allowed before a package becomes unacceptable. The calibration signal may have allowed ±5% and this reduction in the tolerance may affect the size and shape of the calibration signal. Similarly, a fluctuation of up to 5% may be acceptable in the water content, but only 2% allowed in the calibration signal. The effect of such variables may be held in secondary memories within the computer based upon theoretical calculations of their effect. Alternatively, the memory may hold a number of signals from packages containing materials made up to the amended variable and the operator superimposes those signals upon one another to achieve a composite calibration signal reflecting each variable amended. As each amendment is made, the visual display of the amended calibration signal is displayed and the operator can readily see the effect of the amendment in relation to the observed signal and can reject amendments which are impractical or which result in excessively tight tolerances between the calibration and observed signals.

As indicated above, the computer memory may also contain the characteristic signals for known contaminants at different concentrations. The operator may superimpose these upon the reference signal initially obtained for an acceptable product so as to determine the effect of one or more specified impurities on a reference signal when establishing an acceptable calibration signal. Alternatively, as described above, such characteristic signals can be superimposed upon a calibration signal for a given product to identify what contaminant caused rejection of a specific package.

The computer may also interface with a printer or other data reproduction or transfer means whereby the observed and calibration signals for random samples in a production run can be printed out to provide permanent records for audit or other purposes. Alternatively, the computer can be linked by modem or other means to a central record or control location, for example a central process control room whereby a remote operator can control and monitor the operation of two or more process or packaging lines.

Accordingly, the present invention also provides a metal detector associated with a computer programmed to present a signal from the metal detector as a graphic display upon a visual display unit and to accept input from a keyboard or other data input device so as to modify the form of the signal displayed on the visual display unit.

The invention can be applied to a wide range of products to monitor the presence of a wide range of contaminants in those products. For example, it can be used to monitor variations in the electrolyte content of foodstuffs or conductive inks for continuous jet ink jet printers, where one is monitoring fluctuations in one or more desirable components of the contents of a package; or to monitor the presence of undesirable components such as metal objects in a foodstuff, lubricating oil, pharmaceutical product, detergent powder or the like.

The invention has been described above in terms of a package containing a product, and the package can take a wide range of forms. For example, it may be a glass or plastic bottle containing fluid or particulate materials, or a cardboard or other carton containing frozen or other solid foodstuffs. It may also be possible to scan products in open topped aluminum or other metal foil containers by scanning the container from above and using a metal mask to screen out the effect of the side walls of the container on the metal detector. However, the invention can also be applied to other objects, for example solid blocks of frozen foods, fruits, bread and other bakery products which are not contained in a wrapper or package.

DESCRIPTION OF THE DRAWINGS

The invention will now be described by way of illustration to a preferred embodiment thereof as shown in the accompanying drawings, in which.

DESCRIPTION OF THE PREFERRED EMBODIMENTS

Figure 1:
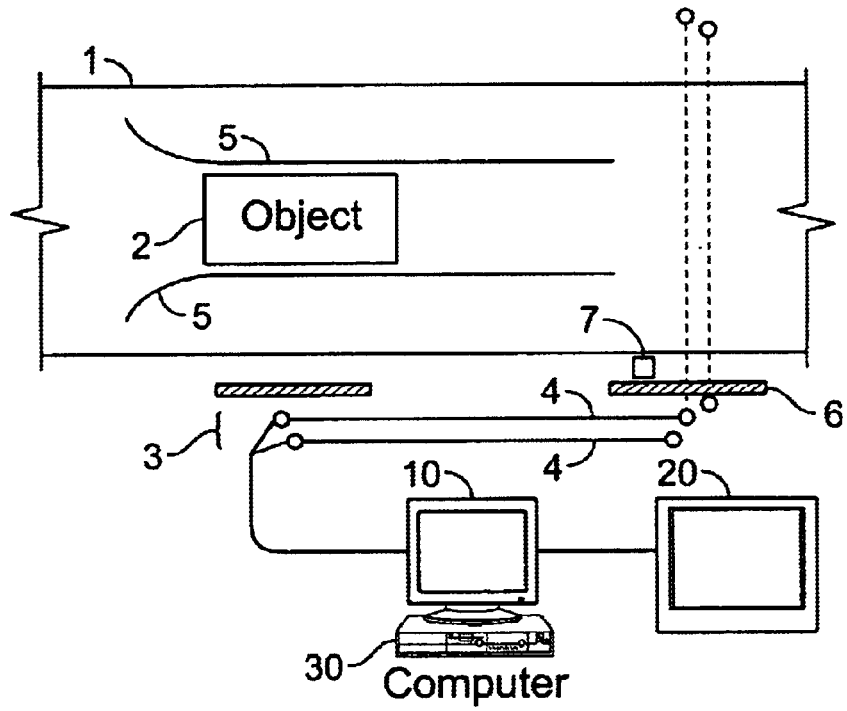
FIG. 1 is a diagrammatic block diagram of the apparatus of the invention.

The apparatus of the invention comprises a belt or roller conveyor system 1 for transporting objects 2 past a metal detector 3. Typically, the detector 3 is a conventional twin coil commercially available detector positioned with its coils 4 orientated with their planes substantially parallel to the line of travel of objects past the detector 3. However, the coils may be orientated with their planes normal to the line of travel as shown dotted in FIG. 1, so that the objects pass through the hoops of the coils in a direction generally transverse to the plane of the coils. It is not necessary that the line of travel in this case be along the axis of the coils, but could be off set radially from that axis. The conveyor 1 is provided with guide rails 5 to position the objects correctly with respect to their orientation to and distance from the detector 3. It is also preferred to provide a solid or mesh metal screen 6 between the detector 3 and the conveyor 1 having a rectangular or other shaped aperture therein through which the detector scans the central portion of the object 2. A photocell 7 detects when the leading edge of the object 2 is at such a position in its travel past the detector 3 that the central portion of the object 2 is in register with the aperture in the screen 6.

Detector 3 is connected to a computer 10, which is in turn connected to a visual display unit (VDU) 20, and to a keyboard 30. The computer is provided with a full graphics program whereby the signals from the detector 3 can be displayed as graphic images on the screen of the VDU. The computer 10 is provided with one or more memory chips or other look up or similar memory units for storing signals from the detector 3; and is programmed to accept input data or instructions from keyboard 30 so as to call up memory signals and to vary those in accordance with the data or instruction from the keyboard.

Figure 2:
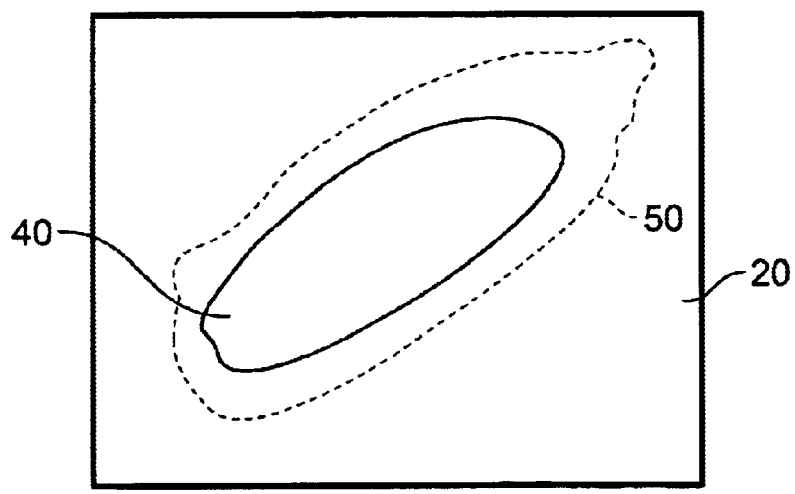
FIG. 2 is a diagrammatic representation of the images displayed on the visual display unit of FIG. 1.

In operation, an object 2 is transported past the detector 3. This actuates the photocell 7 which causes detector 3 to scan the portion of the object exposed to it through the aperture in screen 6 and to send a signal corresponding to the metal contamination of the object to the computer 10. The operator has identified the type of object which is being scanned to the computer by keying in the appropriate identifying codes at keyboard 30. As a result, the computer generates a visual display of both the observed signal 40 from detector 3 and the appropriate calibration signal 50 from its memory, as shown in full line and dotted images respectively in FIG. 2. If desired, the computer can also be programmed to carry out an autoset optimisation of the calibration signal in which a series of observed signals are averaged and the permitted tolerances applied to that average signal to generate a modified calibration signal.

The operator can also amend the calibration signal by applying changes to the tolerances for the nature of the product and observing the effect that each incremental change has on the displayed calibration signal. He can readily observe when a change causes an unacceptable calibration signal, either because part or all of the calibration signal lies within the observed signal and would give rise to persistent rejection of the objects as being contaminated; and/or because the envelope of the amended calibration signal lies so far outside the envelope of the observed signal that excessive amounts of contaminants could be present before the envelope of the calibration signal was breached. The operator can thus interactively amend the calibration signal and observe the results of that amendment on line whilst a signal from the object is being generated for comparison purposes.

The invention has been described above in terms of the observed signal lying within the envelope of the calibration signal. However, there may be cases where the calibration signal lies within the envelope of the observed signal because the expected contaminant causes contraction of the observed signal rather than expansion or tilting of the phase angle of the signal. In this case the system will be set to respond to an excessive contraction of the signal relative to the calibration signal. The invention thus detects when the contamination in an object causes the observed signal to deviate by an unacceptable amount from the calibration signal.

What is claimed is:

1. Apparatus for detecting contamination of an object by a metal or other electrolyte, which apparatus comprises a metal detector associated with a computer programmed to present a signal from the metal detector upon a visual display unit and to accept input from a keyboard or other data input device so as to modify the form of the signal displayed on the visual display unit, characterized in that it comprises:

a mechanism for transporting the object relative to a scanning station at which the object is to be scanned;

a metal detector located at the scanning station and adapted to scan the object and to generate an observed signal corresponding to the effect of the contamination present in the object on the signal generated from the metal detector;

computer means for comparing the observed signal from the metal detector with a calibration signal corresponding to an object having an acceptable level of contamination, and for identifying when an observed signal received from the metal detector deviates by an unacceptable amount from that calibration signal;

display means for displaying in visual graphical form the observed signal from the metal detector and the calibration signal; and means for use by an operator for varying the calibration signal displayed on the display means.

2. Apparatus as claimed in claim 1, characterized in that the metal detector comprises at least two coils through at least one of which a varying or pulsed current is to flow and the effect of the object on the inductive coupling between the coils generates the signals which are to be displayed by the display means.

3. Apparatus as claimed in claim 1, characterized in that a metal or other screen is located between the metal detector and the line of travel of the object past the metal detector and there is an aperture in the screen through which the metal detector is adapted to scan a selected part of the object.

4. Apparatus as claimed in claim 1, characterized in that the means to be used by an operator to vary the calibration signal is a keyboard.

5. Apparatus as claimed in claim 1, characterized in that the computer means is programmed to display both the calibration and observed signals on the visual display means whereby an operator can visually observe the effect of varying the calibration signal in relation to the observed signal so as to permit interactive and/or on line optimization of the calibration signal with respect to the observed signals for products which contain an acceptable level of a contaminant.

6. Apparatus as claimed in claim 1, characterized in that one or more machine readable memories are provided which contain signals from the metal detector for a series of different objects to be passed through the scanning station, whereby the operator can select the calibration signal to be compared to the observed signal for a plurality of different objects.

7. Apparatus as claimed in claim 1, characterized in that one or more machine readable memories are provided which contain signals from specific metal or other electrolyte contaminants, whereby the operator can assess the effect of the presence of such a contaminant in the object upon the calibration signal.

8. Apparatus as claimed in claim 1, characterized in that means are provided for displacing the object from the transport mechanism where the observed signal from that object deviates from the calibration signal by an unacceptable amount.

9. Apparatus as claimed in claim 1, characterized in that the computer means is programmed to compare the observed signal against one or more machine readable memory means so as to identify the nature and/or amount of any contamination which causes the observed signal to deviate from the calibration signal by an unacceptable amount.

10. Apparatus as claimed in claim 1, characterized in that the computer means is programmed to display the signal from the metal detector as a loop-like display on the display means, which signal has a characteristic form and orientation for the object being observed, the envelope for one such display for the calibration signal containing the envelope for the display of the observed signal or vice versa.

11. A method for adjusting the calibration signal for an acceptable object using the apparatus of claim 1, characterized in that an operator views the displays of one or more of the observed signals from the metal detector scanning one or more objects containing an acceptable level of a contaminant and the calibration signal for that object; and adjusts the calibration signal by inputting control data from the keyboard or other input means so as to optimize the calibration signal relative to the observed signal(s).

12. A method as claimed in claim 11, characterized in that the calibration and observed signals are displayed simultaneously and the operator optimizes the differences between the envelopes of the signals displayed.

13. A system for detecting contamination of an object by a metal or other electrolyte, comprising:
- a metal detector located at the scanning station and adapted to scan the object and to generate an observed signal corresponding to the effect of the contamination present in the object on the signal generated from the metal detector;
- a computer for comparing the observed signal from the metal detector with a calibration signal corresponding to an object having an acceptable level of contamination, and for identifying when an observed signal received from the metal detector deviates by an unacceptable amount from that calibration signal; and
- a display unit for displaying in visual graphical form the observed signal from the metal detector and the calibration signal,
- wherein the computer is programmed to display both the calibration and observed signals on the display such that an operator can visually observe the effect of varying the calibration signal in relation to the observed signal so as to permit interactive and/or on-line optimization of the calibration signal with respect to the observed signals for products that contain an acceptable level of a contaminant.

14. The system of claim 13, wherein one or more machine readable memories are provided that contain signals from the metal detector for a series of different objects to be passed through the scanning station, whereby the operator can select the calibration signal to be compared to the observed signal for a plurality of different objects.

15. The system of claim 13, wherein the computer is programmed to display the signal from the metal detector as a loop-like display on the display unit, the signal having a characteristic form and orientation for the object being observed, the envelope for one such display for the calibration signal containing the envelope for the display of the observed signal or vice versa.

16. A method for adjusting the calibration signal for an acceptable object using the system of claim 1, characterized in that an operator views the displays of one or more of the observed signals from the metal detector scanning one or more objects containing an acceptable level of a contaminant and the calibration signal for that object; and adjusts the calibration signal by inputting control data from an input device so as to optimize the calibration signal relative to the observed signal(s).

17. The method of claim 16, characterized in that the calibration and observed signals are displayed simultaneously and the operator optimizes the differences between the envelopes of the signals displayed.

18. A system for detecting contamination of an object by a metal or other electrolyte, comprising:
- a metal detector located at the scanning station and adapted to scan the object and to generate an observed signal corresponding to the effect of the contamination present in the object on the signal generated from the metal detector;
- a computer for comparing the observed signal from the metal detector with a calibration signal corresponding to an object having an acceptable level of contamination, and for identifying when an observed signal received from the metal detector deviates by an unacceptable amount from that calibration signal; and
- a display unit for displaying in visual graphical form the observed signal from the metal detector and the calibration signal,
- wherein the computer is programmed to display the signal from the metal detector as a loop-like display on the display unit, the signal having a characteristic form and orientation for the object being observed, the envelope for one such display for the calibration signal containing the envelope for the display of the observed signal or vice versa.

19. The system of claim 18, wherein one or more machine readable memories are provided that contain signals from the metal detector for a series of different objects to be passed through the scanning station, whereby the operator can select the calibration signal to be compared to the observed signal for a plurality of different objects.

20. A method for adjusting the calibration signal for an acceptable object using the system of claim 18, characterized in that an operator views the displays of one or more of the observed signals from the metal detector scanning one or more objects containing an acceptable level of a contaminant and the calibration signal for that object; and adjusts the calibration signal by inputting control data from an input device so as to optimize the calibration signal relative to the observed signal(s).

* * * * *